United States Patent
Bloczynski et al.

[11] Patent Number: 5,520,786
[45] Date of Patent: May 28, 1996

[54] MEDIATORS SUITABLE FOR THE ELECTROCHEMICAL REGENERATION OF NADH, NADPH OR ANALOGS THEREOF

[75] Inventors: Michael L. Bloczynski; Paul F. Corey, both of Elkhart; Yingping Deng, Granger; Alison J. Murray, Elkhart; Matthew K. Musho, Granger; Hans-Ulrich Siegmund, Elkhart, all of Ind.

[73] Assignee: Bayer Corporation, Elkhart, Ind.

[21] Appl. No.: 471,745

[22] Filed: Jun. 6, 1995

[51] Int. Cl.[6] .............. C25B 11/06; C25B 11/12; C25B 11/14
[52] U.S. Cl. .............. 204/403; 435/817; 401/42; 401/43
[58] Field of Search .............. 429/42, 43; 204/403

[56] References Cited

U.S. PATENT DOCUMENTS 4,490,464  12/1984  Gorton et al. .............. 435/4
4,710,570  12/1987  Thien .............. 544/31
5,373,348  12/1994  Inoue et al. .............. 355/200

OTHER PUBLICATIONS

B. Persson, A Comparative Study of 3,7-Diaminopheonxazine . . . , J. Electroanal. Chem. 292 (1990) 115–138.
Doubova et al., Polyaniline a a Cathode for $O_2$. . . , Electrochimica Acta, vol. 34, No. 3, pp. 337–343, 1989.

Primary Examiner—John Niebling
Assistant Examiner—Alex Noguerola
Attorney, Agent, or Firm—Jerome L. Jeffers

[57] ABSTRACT

Disclosed is an improved electrode suitable for the electrochemical regeneration of the co-enzymes NADH and NADPH. The electrode has imparted on its surface a mediator function which is a 3-phenylimino-3H-phenothiazine or a 3-phenylimino-3H-phenoxazine. Also disclosed is a method of improving the performance of a biochemical fuel cell which operates with a dehydrogenase as a catalyst and a co-enzyme as the energy-transferring redox couple which involves using the improved electrode in the fuel cell.

18 Claims, 3 Drawing Sheets

MEDIATORS SUITABLE FOR THE ELECTROCHEMICAL REGENERATION OF NADH, NADPH OR ANALOGS THEREOF

BACKGROUND OF THE INVENTION

Analytical methods that combine the selectivity of enzymes with the sensitivity of amperometric detection are of interest to the diagnostic industry. The reduction of the nicotinamide co-enzymes (NAD and NADP) is particularly important because they are produced in reactions catalyzed by dehydrogenases. Dehydrogenase catalyzed reactions according to the equation:

play an important role in biological cells and analytical reactions. Several hundred different dehydrogenases are known which selectively catalyze the conversion of different substrates into products. When the substrate, e.g. glucose, is oxidized, the enzymes $NAD^+$ and/or $NADP^+$ are reduced to NADH and NADPH respectively. These co-enzymes are a necessary element in the reaction due to their ability to act with the dehydrogenase enzyme to form an energy-transferring redox couple. The pyridine linked dehydrogenases transfer reversibly two reducing equivalents from the substrate to the oxidized form of the pyridine nucleotide; one of which appears in the reduced pyridine nucleotide as a hydrogen atom, and the other as an electron. The other hydrogen atom removed from the substrate appears as free $H^+$ in the medium.

The co-enzymes $NAD^+$ and $NADP^+$ are expensive chemicals making their regeneration and reoxidation to their original state imperative if they are to be economically used in low cost, disposable, analytical devices.

NADH is oxidized directly at different base electrode materials only with high overvoltages on the order of 1 volt. However, a decrease in this overvoltage can be obtained by the adsorption of functionalities on the electrode surface which mediate the electron transfer from NADH to the electrode. Such mediators are typically selected from materials which may be reoxidized electrochemically without excessive overvoltages rendering them useful as an auxiliary system for electrochemical regeneration. Various mediator compounds suitable for this purpose are known. In U.S. Pat. No. 4,490,464 there are mentioned, by way of background, mediators such as phenazine methosulfate (PMS); phenazine ethosulphate (PES); thionine and 1,2-benzoquinone. This patent goes on to describe electrodes which are modified to catalyze the oxidation of NADH, NADPH or analogs thereof by imparting to the electrode surface as mediator a condensed aromatic ring system comprising at least three and preferably four or more condensed aromatic rings with or without heteroatoms. More particularly, this patent describes the electron exchange with the co-enzyme or analog thereof by structural elements comprising one of either alkyl phenazinium ions, phenazinium ions, phenazinones, phenoxazinium ions, phenoxazinones, phenothiazinium ions or phenothiazinones.

In *J. Electroanal. Chem.* 287, 61–80 (1990) there is disclosed 3-β-naphthoyltoluidine blue O (I):

which is perhaps the most effective of the known phenothiazinium mediators generically disclosed in the '464 patent. A variety of the mediators disclosed in this patent are compared in *J. Electroanal. Chem.* 292, 115–138 (1990).

The phenoxazinium and phenothiazinium ions disclosed in the '464 patent are positively charged species such as (I) above and are readily distinguishable from the mediator compounds of the present invention. The phenoxaziones and phenothiazinones claimed in the '464 patent are 3H-phenothiazines (II) and 3H-phenoxazines (III):

in which the 3-position is derivatized with a carbonyl oxygen group. They bear a structural resemblance to the compounds of the present invention in that the oxygen atoms in (II) and (III) are replaced by nitrogen atom bearing substituted phenyl rings. In reality, however, these compounds are quite different and there is no suggestion in the prior art that replacing the carbonyl oxygen of compounds (II) and (III) with a phenyl-substituted nitrogen atom would afford effective mediators.

The compounds, whose utility as mediators is taught herein, are disclosed in U.S. Pat. No. 4,710,570 which describes the "leuko" or reduced form of these dyes to be "suitable as dye-forming agents in pressure sensitive, thermographic, photothermographic and photographic imaging systems."

U.S. Pat. No. 5,264,092 discloses the mediators of the '464 patent covalently attached to polymers which are useful for the electrochemical regeneration of NADH. This patent discloses a variety of polymeric backbones to which the mediators are attached. Polymer/mediator modified electrodes are also disclosed. Certain of the mediators of the present invention also perform well when immobilized on polymers.

SUMMARY OF THE INVENTION

The present invention involves an electrode suitable for the electrochemical regeneration of the coenzymes dihydronicotinamide adenine dinucleotide (NADH), dihydronicotinamide adenine dinucleotide phosphate (NADPH) or analogs thereof, said electrode having imparted on its surface a mediator function comprising one or more mediator compounds selected from the group consisting of substituted or unsubstituted 3-phenylimino-3H-phenothiazines and 3-phenylimino-3H-phenoxizines.

DESCRIPTION OF THE INVENTION

This invention is predicated on the discovery that 3-phenylimino-3H-phenothiazines and 3-phenylimino-3H-phenoxizine compounds are useful mediators for the electrochemical regeneration (oxidation) of NADH. The mediators of the present invention can be represented by general formulae (IV) and (V).

It is evident that R1 and R2 in formulae IV and V can represent a variety of substituent groups without departing from the scope of the present invention. Such substituent groups are limited only by the ability of one of ordinary skill in the art to prepare stable compounds which have electrochemical properties necessary for the requisite electron transport.

For example, in the above formulae substituents R1 and R2 may be the same or different, and selected from the group consisting of hydrogen, lower alkyl, aryl, halo, haloalkyl, carboxy, carboxyalkyl, alkoxycarbonyl, aryloxycarbonyl, aromatic and aliphatic keto, alkoxy, aryloxy, nitro, dialkylamino, aminoalkyl, sulfo, dihydroxyboron (—B(OH)$_2$) and the like. It is also intended that aliphatic and aromatic groups incorporated into R1 and R2 can themselves bear a variety of substituent groups.

The substituents R1 and R2 may serve to modulate the reduction-oxidation (redox) potential of the mediator, to vary solubility or to function as a handle for covalent attachment of the mediator to a polymer or solid support.

Compounds (IV) and (V) can be represented by a single formula (A) in which the symbol X is used to represent oxygen and sulfur:

Nicotinamide adenine dinucleotide (oxidized form, NAD$^+$; reduced form, NADH) is the cofactor providing chemical redox function for many dehydrogenase enzymes. This cofactor is reduced during the course of the enzymatic reaction as the substrate molecule is oxidized. Amperometric biosensors seeking to use these enzymes as a means to measure substrate concentration correlate this concentration with the current generated as the cofactor is electrochemically re-oxidized. The NADH can be electrochemically re-oxidized on graphite, pyrolytic carbon, glassy carbon, platinum, gold, or a composite made from these materials, electrodes without a mediator, but this reaction occurs with several difficulties including a large overpotential and electrode fouling.

The present invention describes the first use of 3-phenylimino- 3H-phenothiazines (IV) and 3-phenylimino-3H-phenoxizines (V) in the electrochemical regeneration of NADH and NADPH coenzymes or their derivatives and accordingly, encompasses a wide variety of phenothiazine and phenoxazine derivatives. The present mediators can also be used for the electrochemical regeneration of NADH and NADPH derivatives. Derivatives of NADH and NADPH include modified cofactors such as in the case where the coenzyme is attached to a polymer as described by Dolabdjian, et al in *Enzyme Engineering* Vol. 4, G. B. Brown and G. Manecke, eds., Plenum Press, New York, 1978, Pp. 399–400 or covalently attached to the dehydrogenase enzyme as described by M. Persson, et al in *Biotechnology* 9, Pp. 280–284 (1991) or synthetic analogs bearing other substituents so long as they function as the cofactor for the dehydrogenase enzyme. These references are incorporated herein by reference. In a preferred embodiment, the mediator is covalently bonded to Gantrez, i.e. poly(methylvinyl ether-co-maleic anhydride). Gantrez can be represented by the formula where n is preferably from about 120 to about 500.

The mediator compounds useful in this invention are depicted by general formulae IV and V. The structures of the compounds synthesized and tested are numbered with Arabic numerals and appear in the first column of Table 1. Columns 2–7 of Table 1 summarize results of mediator evaluations as described in Examples III and IV.

TABLE 1

| Compound | Mediator Structures and Activities | NADH $E_{ox}^°$ | Titration Potential | on GRE Slope | Glucose $E_{ox}^°$ | Titration on Sensor Potential | Slope |
|---|---|---|---|---|---|---|---|
| 1, Ar-N=C6H4=N-C6H4-Cl (S on Ar) | | 55 mv | 155 mv | 0.0061 | | | |
| 2, Ar-N=C6H4=N-C6H4-N(Et)2 | | 108 mv | 210 mv | 0.0072 | | | |
| 3, Ar-N=C6H4=N-C6H4-Et | | 79 mv / 36 mv | 160 mv / 200 mv | 0.0042 / 0.0125 | | | |
| 4, Ar-N=C6H4=N-C6H4-CF3 | | 62 mv / 101 mv | 162 mv / 200 mv | 0.0077 / 0.0109 | | | |
| 5, Ar-N=C6H4=N-C6H4-CO2CH3 | | 71 mv / 92 mv | 171 mv / 200 mv | 0.0066 / 0.0079 | | | |
| 6, Ar-N=C6H4=N-C6H4-NO2 | | 143 mv / 130 mv | | | | | |

TABLE 1-continued

Mediator Structures and Activities

| Compound | NADH $E_{ox}^°$ | Titration Potential | on GRE Slope | Glucose $E_{ox}^°$ | Titration on Sensor Potential | Slope |
|---|---|---|---|---|---|---|
| 6 — S–C6H4–N=C6H4=N–C6H4–OCH3 (with COCH3 substituent) | 72 mv / 74 mv | 160 mv / 200 mv | 0.0039 / 0.0132 | | | |
| 7 — S–C6H4–N=C6H4=N–C6H4–CO2CH3 | 136 mv | 250 mv | 0.0042 | | | |
| 8 — S–C6H4–N=C6H4=N–C6H4–CO2CH3 (with CF3 substituent) | 141 mv | 250 mv | 0.0056 | | | |
| 9 — S–C6H4–N=C6H4=N–C6H4–(CH2)4CO2H | 24 mv | 100 mv | 0.0059 | | 125 mv | 0.0145 |
| 10 — S–C6H4–N=C6H4=N–C6H4–CH2NH2 | 57 mv | 150 mv | 0.0061 | | 160 mv | 0.0192 |
| 11 — S–C6H4–N=C6H4=N–C6H4–NH2 | 92 mv | 200 mv | 0.0094 | | | |
| 12 — S–C6H4–N=C6H4=N–C6H4–C(O)=N–N=C6H4–NH3 | | | | | | |

TABLE 1-continued

Mediator Structures and Activities

| Compound | NADH $E_{ox}^o$ | Titration Potential | on GRE Slope | Glucose $E_{ox}^o$ | Titration on Sensor Potential | Slope |
|---|---|---|---|---|---|---|
| 13 | 71 mv | 200 mv | 0.0072 | | 150 mv | 0.0185 |
| 14 | −20 mv | 100 mv | 0.0067 | | | |
| 15 | 189 mv & −120 mv | | | −15 mv | 300 mv | 0.0016 |
| 16 | | | | 86 mv | 400 mv | 0.0142 |
| 17 | | | | 138 mv | 100 mv | 0.0156 |
| | | | | | 200 mv | 0.0203 |
| | | | | | 300 mv | 0.0205 |

TABLE 1-continued

Mediator Structures and Activities

| Compound | NADH $E_{ox}^\circ$ | Titration Potential | on GRE Slope | Glucose $E_{ox}^\circ$ | Titration on Sensor Potential | Slope |
|---|---|---|---|---|---|---|
| 18 (S,N ring fused with quinone-N-phenyl-3,5-dicarboxylic acid) | 27 mv | 200 mv | 0.0090 | −14 mv | 100 mv / 300 mv | 0.0848 / 0.0962 |
| 19 (S,N ring fused with quinone-N-phenyl-4-carboxylic acid) | | | | | | |
| 20 (O,N ring fused with quinone-N-phenyl-3,5-dicarboxylic acid) | | | | −116 mv | 100 mv | 0.079 |
| 21 (S,N ring fused with quinone-N-phenyl-2,4-disulfonic acid) | | | | | | |

Among those phenothiazines and phenoxazines which have been prepared and found to have suitable properties as NADH mediators are 3-(4'-chloro-phenylimino)-3H-phenothiazine, 3-(4'-diethylamino-phenylimino)-3H-phenothiazine, 3-(4'-ethyl-phenylimino)-3H-phenothiazine, 3-(4'-trifluoromethyl-phenylimino)-3H-phenothiazine, 3-(4'-methoxycarbonyl-phenylimino)- 3H-phenothiazine, 3-(4'-nitro-phenylimino- 3H-phenothiazine, 3-(4'-methoxy-phenylimino)- 3H-phenothiazine, 7-acetyl-3-(4'-methoxycarbonylphenylimino)- 3H-phenothiazine, 7-trifluoromethyl-3-(4'-methoxycarbonyl-phenylimino)-3H-phenothiazine, 3-(4'-ω-carboxy-n-butyl-phenylimino)-3H-phenothiazine, 3-(4'-aminomethyl-phenylimino)-3H-phenothiazine, 3-(4'-(2"-( 5"-(p-aminophenyl)-1,3,4-oxadiazoyl)phenylimino)-3H-phenothiazine, 3-(4'-β-amino-ethyl-phenylimino)-3H-phenothiazine, 6-(4'-ethylphenyl)amino-3-(4'-ethylphenylimino)- 3H-phenothiazine, 6-(4'-[2-(2-ethanoloxy)ethoxy]-ethoxyphenyl)amino- 3-(4'-[2-(2-ethanoloxy)ethoxy]ethoxyphenylimino)- 3H-phenothiazine, 3-(4'-[2-(2-ethanoloxy)ethoxy]ethoxy-phenylimino)-3H-phenothiazine, 3-(4'-phenylimino)- 3H-phenothiazineboronic acid, 3-(3',5'-dicarboxy-phenylimino)- 3H-phenothiazine, 3-(4'-carboxyphenylimino)- 3H-phenothiazine, 3-(3', 5'-dicarboxy-phenylimino)- 3H-phenoxazine, 3-(2',5'-phenylimino)-3H-phenothiazinedisulfonic acid, and 3-(3'-phenylimino)-3H-phenothiazinesulfonic acid.

The method of practicing the invention is further illustrated by the following examples.

EXAMPLE I (Synthesis of Mediators)

In general, the synthesis of the compounds useful as mediators in the present invention involves the oxidative coupling of an aniline with a phenothiazine or a phenoxazine. The synthesis of the unsubstituted 3-phenylimino-3H-phenothiazine was reported in *Liebigs Ann. Chemn.* 322, 39 (1902) whereas the synthesis of two other analogs is reported in U.S. Pat. No. 4,710,570. Both of these references are incorporated herein by reference. The general synthetic scheme for preparing these compounds is presented in Scheme I in which compound 18 from Table I is exemplified:

Scheme I

The synthesis of specific compound from Table I (compounds 4, 12 and 20) was carried out as follows:

3-(4'-trifluoromethylphenylimino)-3H-phenothiazine
(4)

Phenothiazine (2.0 g, 10 mmole) and 4-aminobenzotrifluoride (1.77 g, 11 mmole) were dissolved in methanol (MeOH) (100 mL) with warming to 45° C., treated with a solution of $I_2$ (5.0 g, 19.4 mmole) in MeOH (80 mL) in one portion and allowed to stir for 3 h at 45° C. The reaction mixture was filtered and the collected solid was washed with MeOH (100 mL). The solid was dissolved in $CHCl_3$ (60 mL) containing triethylamine ($NEt_3$) (6 mL) then this solution was diluted with hexane (200 mL) and chilled in an ice bath for 2 h. The purple solid that separated was collected by filtration and redissolved in $CHCl_3/NEt_3$ (10:1, v:v) (50 mL) and chromatographed on silica gel (250 g) using $CHCl_3$/acetone (96:4, v:v) development. The purple product band was collected and evaporated to dryness in vacuo to afford 4 (0.26 g, 7.3%) with mp=207°–8° C.

Anal. Calcd. for $C_{19}H_{11}N_2F_3S$: C, 63.84; H, 3.38; N, 7.84. Found: C, 63.69; H, 3.26; N, 7.84.

3-(3',5'-Dicarboxyphenylimino)-3H-phenothiazine
(18)

Phenothiazine (1.0 g, 5.0 mmol) and 5-aminoisophthalic acid (0.9 g, 5.0 mmol) were dissolved in MeOH (200 mL), cooled to 10° C. and treated with 1 M aqueous $AgNO_3$ (30 mL, 30 mmol). After stirring at 10° C. for 30 minutes $H_2O$ (40 mL) was added and stirring continued for an additional 5 minutes. The solid product was then collected by filtration and washed with $H_2O$ (50 mL). The solid was dissolved in MeOH (500 mL) containing concentrated aqueous $NH_4OH$ (10 mL), stirred for 20 minutes then filtered to remove Ag. The filtrate was concentrated to ca. half its original volume under reduced pressure and refrigerated overnight at 5° C. The mixture was then filtered through Celite (Celite Corp.) and concentrated in vacuo until solid began to separate. The resulting solution (ca. 100 mL) was again filtered through Celite, diluted with ethyl acetate (900 mL) and allowed to stand for 15 minutes. The red solid that separated was collected by filtration, washed with ethyl acetate and dried to give 18(1.55 g, 82.5%).

3-(3',5'-Dicarboxyphenylimino) 73H-phenoxazine
(20)

Phenoxazine (0.92 g, 5 mmole) was dissolved in tetrahydrofuran (THF) (10 mL) and stirred at ambient temperature with a solution of 5-aminoisophthalic acid (0.88 g, 4.86 mmole) in $H_2O$ (10 mL) containing concentrated aqueous $NH_4OH$ (1 mL). The mixture was rapidly treated with a solution of 1.0 M aqueous $AgNO_2$ solution (13.5 mL) and stirred for 2 h, during which time a solid separated. The solid was collected by filtration and extracted three times with THF (100 mL each). The combined extracts were evaporated to dryness in vacuo to yield a dark solid (0.8 g) which was taken up in $CHCl_3/MeOH$ (1:1, v:v) (100 mL), with warming, and chromatographed on silica gel (300 g) using $CHCl_3$/MeOH (2:1, v:v) development. The dark orange product band was collected and evaporated to dryness in vacuo to afford 20(0.30 g, 16.7%).

Using the procedures outlined above, one skilled in this art could synthesize a wide variety of substituted analogs of these compounds.

EXAMPLE II (Synthesis of Polymer-Bound Mediators)

The synthesis of a polymeric mediator, designated herein as P-3, is representative of the method used to prepare other polymer bound mediators within the scope of the present invention. This synthesis is illustrated in Scheme 2 and the description which follows it. P-3 may be described as "40% 13 on Gantrez" because 40% of the anhydride groups on the polymer have been reacted with the amino moiety of 13.

polishing the electrode's surface first using a fine grit sandpaper then a suspension of ≧1 micron alumina particles. A 1–2 mM solution of the mediator in methanol was prepared and the electrode soaked in this solution for 2 minutes. The electrodes were then rinsed with water and Scheme 2

40% 13 on Gantrez (P-3)

A solution of GANTREZ AN-119 (ISP Technologies, Inc., Wayne, N.J.) (0.156 g, 1.0 mmol anhydride) in anhydrous N,N-dimethylformamide (DMF) (10.0 mL), maintained under an inert gas atmosphere at ambient temperature, was treated at once with a solution of 13 (0.1326 g, 0.4 mmole) and anhydrous triethylamine 0.56 mL, 4.0 mmole) in anhydrous DMF (5.0 mL). Additional DMF (3.0 mL) was used to rinse in traces of the 13 solution then the reaction mixture was allowed to stir for 1 hour. The mixture was diluted with $H_2O$ (25 mL), stirred for 15 minutes then blended into additional $H_2O$ (175 mL). The resulting solution was acidified with conc. HCl (3.0 ML) whereupon the product separated as a solid. The mixture was centrifuged for 20 min. at 10,400 X g and the supernatant discarded. The pellet was resuspended in 0.1 M HCl (20 mL) with sonication and centrifuged for 20 min. at 33,400 X g. The supernatant was discarded and the pellet resuspended in 100% ethanol (20 mL) with sonication, then centrifuged for 30 min. at 33,400 X g. The supernatant was discarded and the pellet was dried in vacuo to afford P-3 (0.26 g) as a black powder.

Polymeric mediators P-1 (20% 11 on Gantrez) and P-2 (20% 13 on Gantrez) are prepared analogously to P-3 except that the 0.4 mmol of 13 is replaced with 0.2 mmol of 11 or 0.2 mmol of 13 respectively.

EXAMPLE III (Evaluation of Mediators on Graphite Electrodes)

Graphite rod electrodes (3 mm in diameter from Johnson Matthey Electronics, Ward Hill, Mass.) were prepared by soaked for a short time in 0.25 M phosphate buffer (pH=7.0). A current vs. voltage profile was first run to determine the cathodic and anodic peak positions vs. a Ag/AgCl reference electrode. Currents were then measured in pH=7.0 solutions containing NADH in concentrations from 20 to 200 μM, using a potential that was typically 100 mv more positive than the oxidative peak potential ($E°_{ox}$) obtained in the cyclic voltammetry experiment above (actual potentials used are listed in column #3 of Table 1), and the slope of the line obtained from a least squares fit of the current vs. NADH concentration data gave the relative sensitivity of each mediator in μA/μM NADH. These slopes for various mediators are listed in the 4th column of Table 1; the greater the slope the better the mediator. For comparison, the slope obtained for 3-β-naphthoyl-toluidine blue O (I) under these conditions is 0.0075.

EXAMPLE IV (Evaluation of Mediators on Printed Electrodes)

Experiments involving printed electrodes comprising a printed sensor card with a graphite/carbon working electrode and a silver/silver chloride reference electrode were carried out. The ink used for the graphite/carbon electrode was No. 423SS (from Acheson Colloids Co., Port Huron, Mich.) and No. 427SS silver ink (same vendor) blended with 15–25% AgCl for the silver/silver chloride reference electrode. Electrode surface area was 0.03 $cm^2$.

Figure 1:
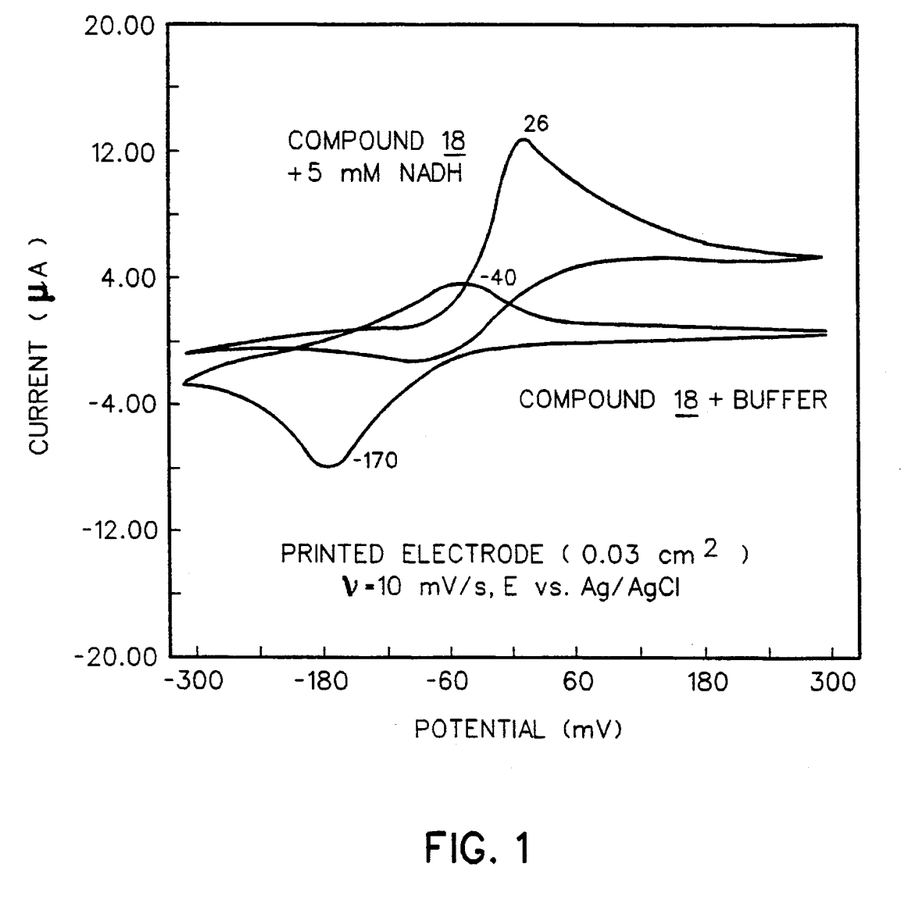
FIG. 1 represents the cyclic voltammogram of 0.6 mM compound 18 in 0.6 mM PIPES buffer at pH=7.0 alone and in the presence of 5 mM NADH.
Figure 2:
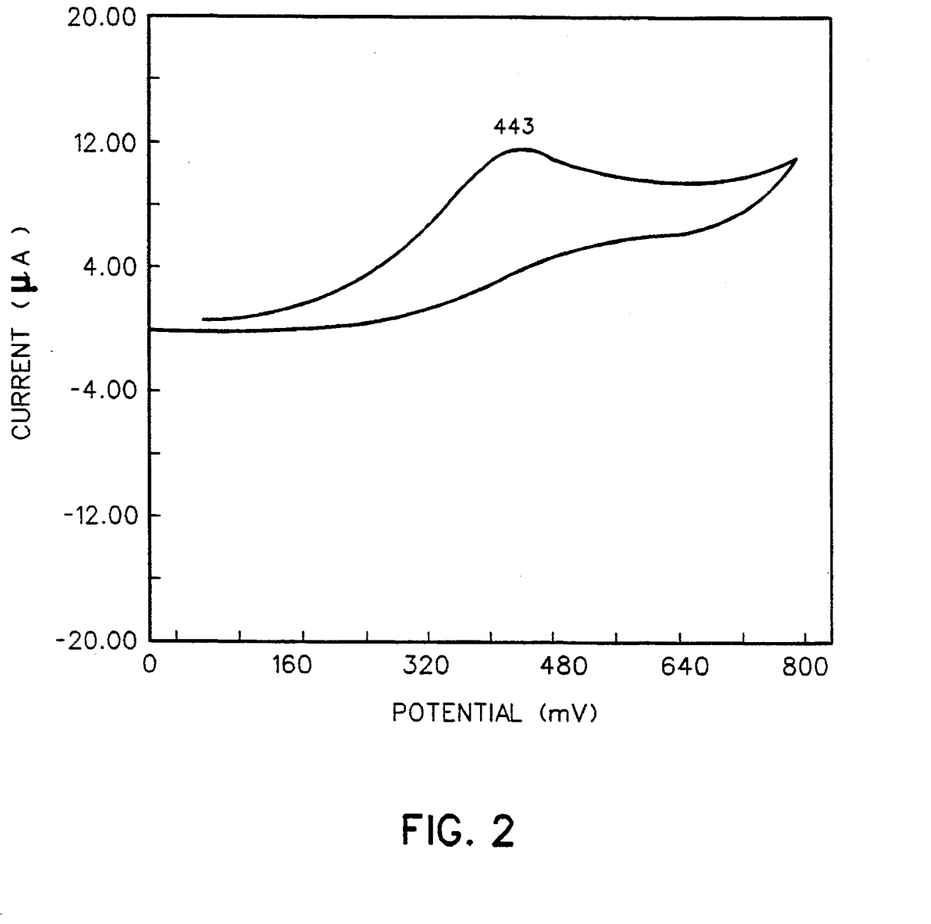
FIG. 2 shows a typical cyclic voltammogram of NADH being oxidized directly on a printed electrode.

Cyclic voltammetry experiments were performed on printed electrodes just as on the graphite rod electrodes. FIG. 1 shows the cyclic voltammogram of 0.6 mM compound 18 in 0.6 mM PIPES buffer at pH=7.0 alone and in the presence of 5 mM NADH. The increase in current at a potential of 26 mv in the presence of NADH is due to the oxidation of mediator that had been reduced by NADH. The mediator is reduced as it oxidizes NADH to $NAD^+$ and is then re-oxidized electrochemically at the electrode. In effect the mediator facilitates the electrochemical oxidation of NADH at potentials considerably lower than those required to oxidize NADH directly. FIG. 2 shows a typical cyclic voltammogram of NADH being oxidized directly (no mediator) on a printed electrode. A much higher peak potential (443 mv) is apparent.

A biosensor for measuring glucose concentration uses the enzyme glucose dehydrogenase to reduce $NAD^+$ to NADH as it oxidizes glucose to gluconolactone. Mediated electrochemical re-oxidation of the NADH to $NAD^+$ generates a current that is proportional to the glucose concentration.

A typical glucose biosensor was fabricated as follows: A solution of 4 mM mediator in 100 mM pH= 7.0 phosphate buffer containing 25 mM KCl was prepared and diluted with an equal volume of a solution composed of 1.96 g 5% Surfynol (Air Products and Chemicals, Inc., Allentown, Pa.), 0.32 g NAD, 0.70 g Glucose Dehydrogenase GDH (Toyobo), 1.44 g 0.5M PIPES buffer pH—7.0 and 5.5 mL DI $H_2O$. 1.75 μL of the mixture was applied to the sensor area and allowed to dry at RT for about 20 min. The electrode was assembled in a format having a small capillary gap, treated with a solution of aqueous glucose and the current measured at the potential noted in the 6th column of Table 1. This was done for samples containing glucose concentrations of 0, 50, 100, 200 and 500 mg/dL and the slope of the lisine line obtained from a least squares fit of the current vs. glucose concentration data gave the relative sensitivity of each mediator in $\mu A/mg\ dL^{-1}$ glucose; the larger the slope the better the mediator. These slopes are listed in the last column of Table 1.

Figure 3:
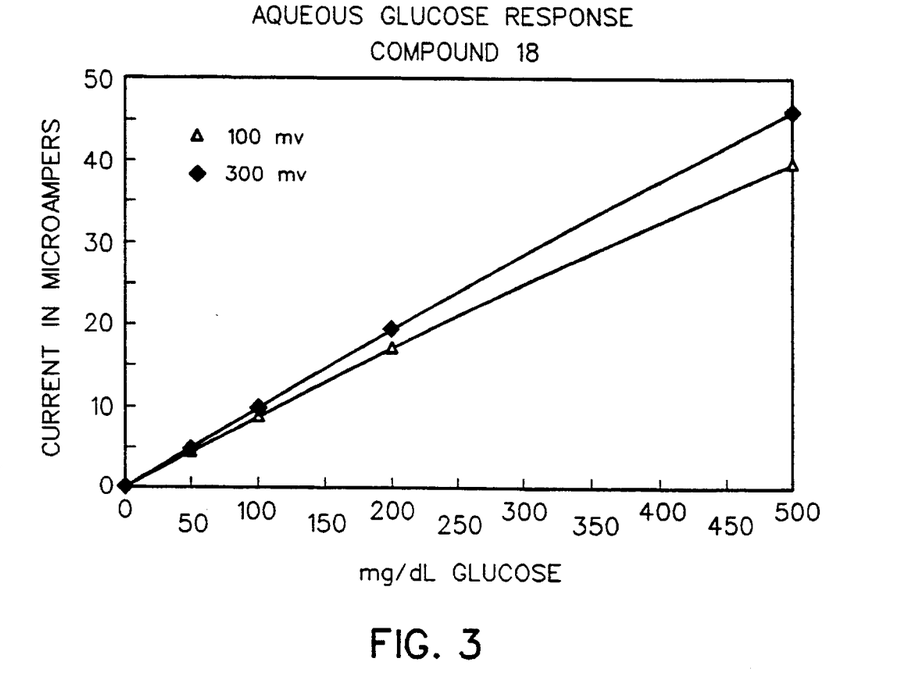
FIG. 3 is a plot of current vs. glucose concentration at set potentials for one of the mediators of the present invention.

FIG. 3 shows the plot of current vs. glucose concentration for compound 18 at 100 mv and 300 mv potentials.

Polymeric mediators were incorporated into complete glucose biosensors as described above and the relative sensitivities are listed in the last column of Table 2.

TABLE 2

Activity of Polymeric Mediators

| | NADH $E°_{ox}$ | Titration Potential | on GRE | Glucose $E°_{ox}$ | Titration Potential | on Sensor Slope |
|---|---|---|---|---|---|---|
| P-1 (20% 11 - Gantrez) | | | −26 mv | | 100 mv 300 mv | 0.0204 0.0362 |
| P-2 (20% 13 - Gantrez) | | | −62 mv | | 300 mv | 0.0276 |
| P-3 (40% 13 - Gantrez) | | | −43 mv | | 300 mv | 0.0217 |

Figure 4:
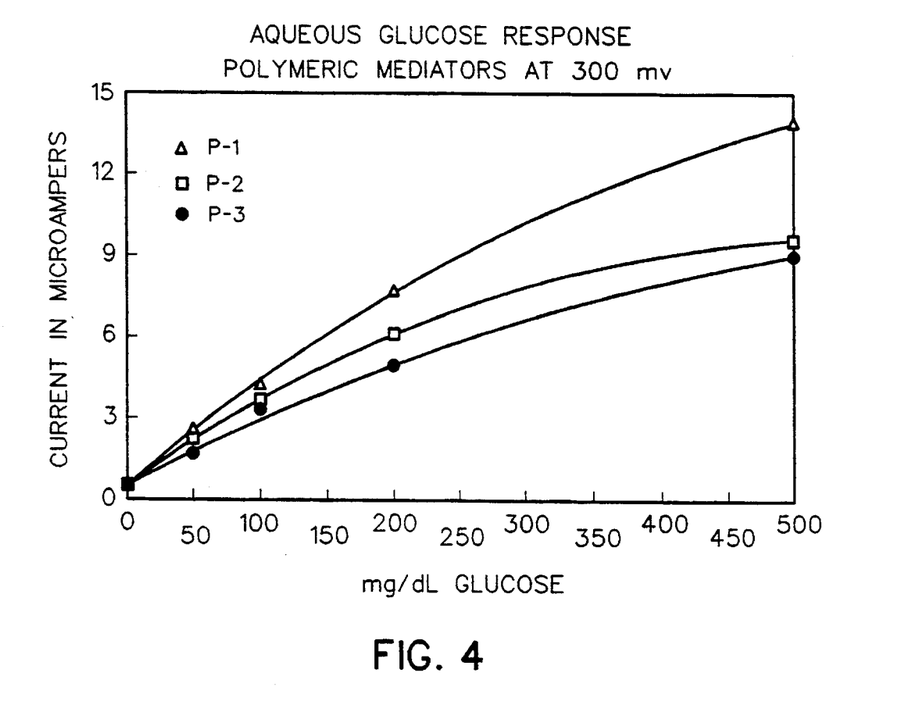
FIG. 4 is a plot of current vs. glucose potential using polymeric mediators.

FIG. 4 shows the plot of current vs. glucose concentration for 3 polymeric mediators at 300 mv potential.

What is claimed is:

1. An electrode for the electrochemical regeneration of the coenzymes dihydronicotinamide adenine dinucleotide (NADH), dihydronicotinamide adenine dinucleotide phosphate (NADPH) or analogs thereof characterized in that there has been imparted to the electrode surface a mediator function comprising one or more mediator compound selected from the group of substituted or unsubstituted 3-phenylimino-3H-phenothiazines and 3-phenylimino-3H-phenoxazines.

2. An electrode as in claim 1 wherein the mediator is characterized by Formula I or Formula II:

wherein R1 and R2 are substituents which serve to modulate the reduction-oxidation (redox) potential of the mediator, to vary the mediator's solubility or to function as a site for the covalent attachment of the mediator to a polymer or solid support.

3. The electrode of claim 2 wherein R1 and R2, which may be the same or different, are selected from the group consisting of hydrogen, lower alkyl, aryl, halo, haloalkyl, carboxy, carboxyalkyl, alkoxycarbonyl, aryloxycarbonyl, aromatic and aliphatic keto, alkoxy, aryloxy, nitro, dialkylamino, aminoalkyl, sulfo and dihydroxyboron wherein the aliphatic and aromatic groups are substituted or unsubstituted.

4. The electrode of claim 1 wherein the electrode material is graphite, pyrolytic carbon, glassy carbon, platinum, gold or a composite made from these materials.

5. The electrode of claim 1 wherein the mediator is attached to a polymer.

6. The electrode of claim 5 wherein the polymer is poly(methylvinyl ether-co-maleic anhydride).

7. The electrode of claim 1 wherein the mediator is selected from the group comprised of:

3-(4'-chloro-phenylimino)-3H-phenothiazine, 3-(4'-diethylamino-phenylimino)-3H-phenothiazine, 3-(4'-ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxy-phenylimino)-3H-phenothiazine, 7-acetyl-3-(4'-methoxycarbonylphenylimino)-3H-phenothiazine, 7-trifluoromethyl-3-(4'-methoxycarbonylphenylimino)-3H-phenothiazine, 3-(4'-ω-carboxy-n-butyl-phenylimino)-3H-phenothiazine, 3-(4'-aminomethyl-phenylimino)-3H-phenothiazine, 3-(4'-(2"-(5"-(p-aminophenyl)-1,3,4-oxadiazoyl)phenylimino)- 3H-phenothiazine, 3-(4'-β-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl)amino-3-(4'-[2-(2-ethanoloxy)ethoxy-phenylimino)-3H-phenothiazine, 3-(4'-[2-(2-ethanoloxy)ethoxy-phenylimino)-3H-phenothiazine, 3-(4'-phenylimino)-3H-phenothiazineboronic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(2',5'-phenylimino)-3H-phenothiazinedisulfonic acid, and 3-(3-phenylimino)-3H-phenothiazinesulfonic acid.

8. The electrode of claim 7 wherein the mediator is 3-(4'-trifluoromethyl-phenylimino)-3H-phenothiazine.

9. The electrode of claim 7 wherein the mediator is 3-(4'-methoxycarbonyl-phenylimino)-3H-phenothiazine.

10. The electrode of claim 7 wherein the mediator is 3-(4'-ω-carboxy-n-butyl-phenylimino)-3H-phenothiazine.

11. The electrode of claim 7 wherein the mediator is 3-(4'-aminomethyl-phenylimino)-3H-phenothiazine.

12. The electrode of claim 7 wherein the mediator is 3-(4'-β-aminoethyl-phenylimino)-3H-phenothiazine.

13. The electrode of claim 7 wherein the mediator is 3-(3',5'-dicarboxy-phenylimino)-3H-phenothiazine.

14. The electrode of claim 7 wherein the mediator is 3-(3',5'-dicarboxy-phenylimino)-3H-phenoxazine 15. The electrode of claim 7 wherein the mediator is 3-(2',5'-phenylimino)-3H-phenothiazinedisulfonic acid.

16. The electrode of claim 7 wherein the mediator is 3-(3'-phenylimino)-3H-phenothiazinesulfonic acid.

17. The electrode of claim 5 wherein the mediator is 3-(4'-aminomethyl-phenylimino)-3H-phenothiazine or 3-(4'-β-aminoethyl-phenylimino)-3H-phenothiazine.

18. The electrode of claim 6 wherein the mediator is 3-(4'-aminomethyl-phenylimino)-3H-phenothiazine or 3-(4'-β-aminoethyl-phenylimino)-3H-phenothiazine.

* * * * *